(12) United States Patent
Kim

(10) Patent No.: US 10,226,494 B2
(45) Date of Patent: Mar. 12, 2019

(54) **ANTIOXIDANT COMPOSITION CONTAINING EXTRACELLULAR POLYSACCHARIDE PRODUCED USING *CERIPORIA LACERATA* AS ACTIVE INGREDIENT**

(71) Applicant: FUGENBIO CO., LTD., Seoul (KR)

(72) Inventor: Yoon Soo Kim, Seongnam-si (KR)

(73) Assignee: FUGENBIO CO., LTD., Seocho-gu, Seoul (KR)

( * ) Notice: Subject to any disclaimer, the term of this patent is extended or adjusted under 35 U.S.C. 154(b) by 0 days.

(21) Appl. No.: 15/527,741

(22) PCT Filed: Nov. 27, 2015

(86) PCT No.: PCT/KR2015/012845
§ 371 (c)(1),
(2) Date: May 18, 2017

(87) PCT Pub. No.: WO2016/085290
PCT Pub. Date: Jun. 2, 2016

(65) Prior Publication Data
US 2017/0333501 A1 Nov. 23, 2017

(30) Foreign Application Priority Data

Nov. 27, 2014 (KR) .................. 10-2014-0167876

(51) Int. Cl.

| | | |
|---|---|---|
| *A61K 39/00* | (2006.01) | |
| *A61K 38/00* | (2006.01) | |
| *A61K 36/07* | (2006.01) | |
| *A61Q 19/00* | (2006.01) | |
| *A61K 36/06* | (2006.01) | |
| *A23K 20/163* | (2016.01) | |
| *A23L 33/10* | (2016.01) | |
| *A61K 8/9728* | (2017.01) | |
| *A61K 8/73* | (2006.01) | |
| *A61K 31/715* | (2006.01) | |

(52) U.S. Cl.
CPC ............ *A61K 36/07* (2013.01); *A23K 20/163* (2016.05); *A23L 33/10* (2016.08); *A61K 8/73* (2013.01); *A61K 8/9728* (2017.08); *A61K 31/715* (2013.01); *A61K 36/06* (2013.01); *A61Q 19/00* (2013.01); *A23V 2002/00* (2013.01); *A61K 2236/10* (2013.01); *A61K 2236/17* (2013.01); *A61K 2236/30* (2013.01); *A61K 2800/10* (2013.01); *A61K 2800/522* (2013.01)

(58) Field of Classification Search
CPC ........................... A61K 39/00; A61K 39/0002
USPC ............................................ 424/184.1, 274.1
See application file for complete search history.

(56) References Cited

U.S. PATENT DOCUMENTS

2014/0193454 A1    7/2014  Kim

FOREIGN PATENT DOCUMENTS

| KR | 10-1031605 B1 | 4/2011 |
|---|---|---|
| KR | 10-1444614 B1 | 9/2014 |
| WO | 2014/112666 A1 | 7/2014 |
| WO | 2016/010182 A1 | 1/2016 |
| WO | 2016/072710 A1 | 5/2016 |

OTHER PUBLICATIONS

Ji-Eun Kim et al., "Hyperglycemic Effect of Submerged Culture Extract of Ceriporia lacerata in Streptozotocin-induced Diabetic Rats", Food Sci. Biotechnol., 2012, pp. 1685-1693, 21(6).
Tuzz-Ying Song et al., "Antioxidant Properties of Antrodia camphorata in Submerged Culture", J. Agric. Food Chem., 2002, pp. 3322-3327, vol. 50, No. 11.
International Searching Authority, International Search Report for PCT/KR2015/012845, dated Mar. 3, 2016.
German Patent and Trademark Office; communication dated Sep. 10, 2018 in counterpart application No. 11 2015 005 378.6.

*Primary Examiner* — Rodney P Swartz
(74) *Attorney, Agent, or Firm* — Sughrue Mion, PLLC

(57) ABSTRACT

The present invention relates to an antioxidant composition containing an extracellular polysaccharide produced using *Ceriporia lacerata*, or a mycelium culture of *Ceriporia lacerata* comprising the same, or a dry powder or an extract thereof as an active ingredient. The composition can be used as an antioxidant for preventing or treating various diseases such as brain diseases such as stroke, Parkinson's disease, etc., heart diseases, ischemia, arteriosclerosis, skin damage, inflammation, rheumatism, autoimmune diseases, etc. including cancers as well as aging, or as a health functional food, a cosmetic material or a feed composition having an antioxidant effect.

11 Claims, 1 Drawing Sheet

[Fig. 1]
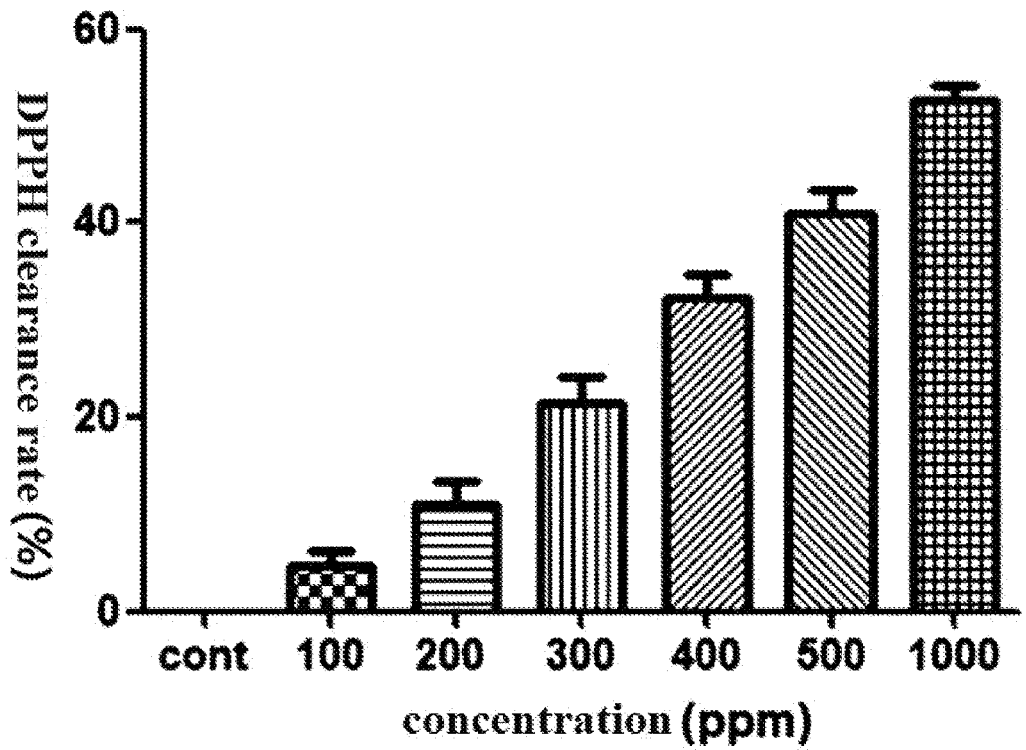
[Fig. 2]
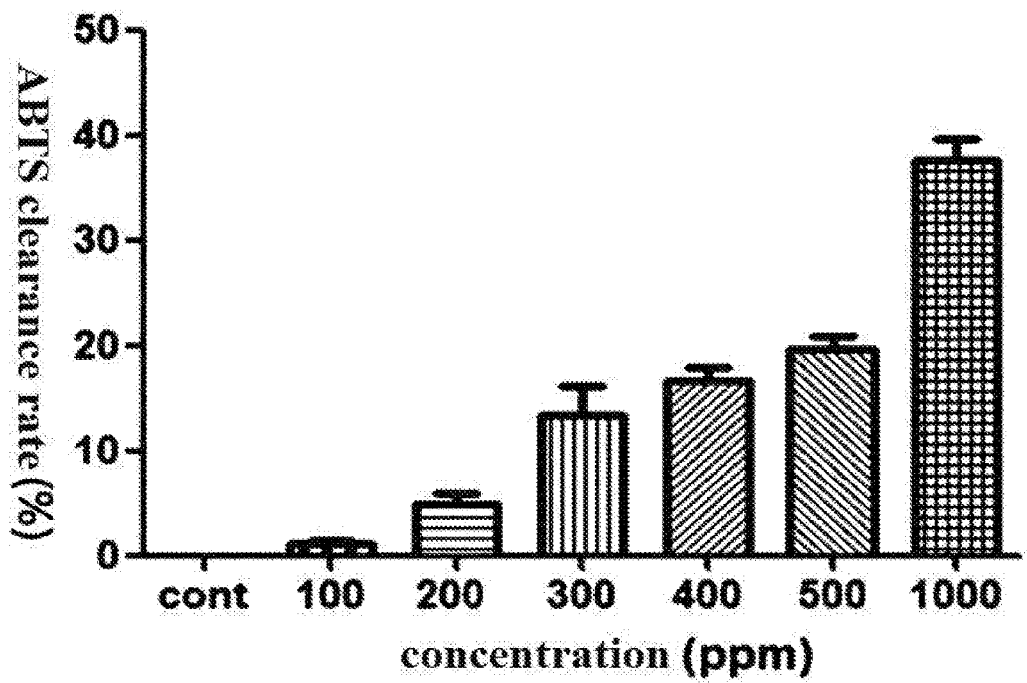

ANTIOXIDANT COMPOSITION CONTAINING EXTRACELLULAR POLYSACCHARIDE PRODUCED USING *CERIPORIA LACERATA* AS ACTIVE INGREDIENT

CROSS REFERENCE TO RELATED APPLICATIONS

This is a National Stage of Application No. PCT/KR2015/012845 filed Nov. 27, 2015, claiming priority based on Korean Patent Application No. 10-2014-0167876 filed Nov. 27, 2014, the contents of all of which are incorporated herein by reference in their entirety.

TECHNICAL FIELD

The present invention relates to an antioxidant composition comprising an extracellular polysaccharide produced by *Ceriporia lacerata*, a mycelial culture medium of *Ceriporia lacerata* containing the same, or dried powders or an extract of the mycelial culture medium, as an effective ingredient.

BACKGROUND ART

Since free radicals are chemically very unstable compounds, they have a strong tendency to take electrons from other compounds around them to become stable compounds. As a result, the molecules around the free radicals easily lose their electrons and get oxidative damage, and also the molecules themselves become free radicals and attack compounds around them, which can take place continuously in a series of reactions. These free radicals are naturally produced through life activities in a human body. Typical free radicals include superoxide radical ($O_2-$), hydroxyl radical (HO.) and hydrogen peroxide ($H_2O_2$) derived from oxygen (stable molecular state of ground state triplet oxygen) which is essential for energy production in order to maintain life, and reactive oxygen species (ROS) such as singlet oxygen ($^1O_2$) which are highly reactive free radicals.

The reactive oxygen species oxidatively damage the fat, protein, and genes that constitute a human body, thereby causing not only aging but also cancer, brain disorders such as stroke and Parkinson's disease, heart disorder, ischemia, arteriosclerosis, skin damage, inflammation, rheumatism, autoimmune disorder, and the like. A human body has antioxidation enzyme system such as superoxide dismutase (SOD), peroxidase, catalase and glutathione peroxidase as a means to protect the human body from these reactive oxygen species. Various environmental factors such as various chemical substances, food additives, smoking, drinking, ultraviolet rays, and pollution-or environmental contamination-caused mental stress destroy the balance of our body to generate an excessive amount of reactive oxygen species than needed for normal life activity of a human body. Such an excessive amount of reactive oxygen species may exceed the body's ability of self-antioxidation protection system, thereby increasing the occurrence of various disorders and speed of aging.

An antioxidation activity refers not only to an ability to prevent excessive production of reactive oxygen in vivo, but an ability to prevent oxidation that causes irreversible damage to cells. The substances which have such antioxidation activity are called antioxidants, and they are divided into synthetic antioxidants which are artificially synthesized, and natural antioxidants that exist in nature. Antioxidants are widely used in various fields such as drugs, food, cosmetics and feed. Examples of synthetic antioxidants developed so far include butylated hydroxyanisole (BHA), butylated hydroxytoluene (BHT), and nordihydroguaiaretic acid (NDGA), etc., and natural antioxidants include antioxidation enzymes such as superoxide dismutase, peroxidase, catalase and glutathione peroxidase, etc., and non-enzymatic antioxidants such as ascorbic acid (vitamin C), tocopherol (vitamin E) and carotenoids. However, long term use of synthetic antioxidants in a human body is restricted because they are not only easily destroyed by heating due to their heat labile property, but also have a disadvantage that their reactive oxygen-elimination effect in vivo is not sufficient and various disorders such as allergy and cancer can be induced in the human body. Therefore, attempts have been actively made to find an antioxidant substance from natural products which has high antioxidation activity but does not show harmful effect on a human body. As the natural antioxidant substances, certain plant extracts such as green tea, *E. senticosus*, ailanthus, chrysanthemum, persimmon leaf, Aurescens, Harlequin glorybowe, wild rosebush, wild rosebush, dandelion, safflower, timber, and the like are known to be effective, and food additives, cosmetic compositions and pharmaceutical compositions using the same have been researched and developed (Korean Patent No. 1258696 and Korean Patent No. 0682319). Despite these efforts, however, there are a myriad of unknown antioxidants in nature. Therefore, the need for research and development of a natural antioxidant substance with better antioxidation activity is increasing day by day.

It is known that *Ceriporia lacerata* is a kind of white-rotting fungus and conducts co-metabolism, i.e., lignin decomposition, in order to use carbon sources such as cellulose, hemi-cellulose, other polysaccharides, and glycerol, etc., in the ecosystem. However, it has not been reported that *Ceriporia lacerata* has excellent antioxidation activity, and the extracts thereof have not been reported to have antioxidation activity.

Accordingly, the present inventors have found that an extracellular polysaccharide produced by *Ceriporia lacerata* or a mycelial culture medium of *Ceriporia lacerata* containing the same, or dried powders or an extract thereof has an antioxidation effect and completed the present invention which is related to a composition for antioxidation comprising the extracellular polysaccharide, the mycelial culture medium, dried powders, or the extract, as an active ingredient.

DISCLOSURE OF INVENTION

Technical Problem

It is an object of the present invention to provide a composition for antioxidation comprising a pharmacologically active ingredient produced by *Ceriporia lacerata*.

It is another object of the present invention to provide an additive having antioxidation effect, comprising a pharmacologically active ingredient produced by *Ceriporia lacerata*.

Solution to Problem

In accordance with one object of the present invention, there is provided a composition for antioxidation comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided an additive for antioxidation comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

In accordance with another object of the present invention, there is provided a method for antioxidation comprising administering to a subject in need of antioxidation capacity an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

In accordance with another object of the present invention, there is provided a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium for preparing a drug for antioxidation.

Advantageous Effects of Invention

A composition comprising an extracellular polysaccharide produced by *Ceriporia lacerata* or a mycelial culture medium of *Ceriporia lacerata* containing the same, or dried powders or an extract thereof, as an effective ingredient, shows excellent antioxidation activity, and thus it can be usefully employed as a pharmaceutical composition for preventing and treating various disorders, a health functional food composition, a functional cosmetic composition, or an animal feed, or an additive for antioxidation.

BRIEF DESCRIPTION OF DRAWINGS

FIG. 1 is a graph showing DPPH (1,1-diphenyl-2-pycryl-hydrazyl) elimination activity of an extracellular polysaccharide produced by *Ceriporia lacerata*.

FIG. 2 is a graph showing ABTS (2,2'-azinobis(3-ethyl-benzothiazoline-6-sulfonic acid)) elimination activity of an extracellular polysaccharide produced by *Ceriporia lacerata*.

BEST MODE FOR CARRYING OUT THE INVENTION

Hereinafter, the present invention is explained in detail.

In the present invention, there is provided a composition for antioxidation, which contains an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

The composition for antioxidation of the present invention can be used in various fields such as drugs, foods, cosmetics and feed, etc.

In a composition according to the present invention, the extracellular polysaccharide may comprise about 40 to 60 wt % of sugar and about 30 to 40 wt % of protein, about 40 to 50 wt % of sugar and about 32 to 38 wt % of protein, or about 43 to 47 wt % of sugar and about 33 to 36 wt % of protein, preferably about 45 wt % of sugar and about 34 wt % of protein.

The sugar may include mannose, galactose and glucose.

The extracellular polysaccharide may have a molecular weight of about 100 to 150 kDa, about 110 to 140 kDa or about 115 to 125 kDa, preferably about 120 kDa.

According to one preferred embodiment of the present invention, the extracellular polysaccharide may be prepared by a preparation method comprising the steps of: (a) culturing mycelia of *Ceriporia lacerata* in a liquid to prepare a mycelial culture medium of *Ceriporia lacerata*, (b) drying the mycelial culture medium of *Ceriporia lacerata* to form powders, and (c) extracting the powders of the mycelial culture medium of *Ceriporia lacerata* with a solvent, and filtering and concentrating the resultant extract under reduced pressure.

The medium for culturing in a liquid in step (a) may contain sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water, and the hydrogen ion concentration (pH) of the medium may be 4.5 to 6.0.

According to one preferred embodiment of the present invention, the medium may contain 0.2 to 3 wt % of sugar, 0.2 to 3 wt % of glucose, 0.2 to 4 wt % of starch, 0.1 to 0.5 wt % of sorghum powder, 0.1 to 0.5 wt % of barley powder, 0.2 to 3 wt % of soybean flour, 0.05 to 0.1 wt % of magnesium sulfate ($MgSO_4$), 0.05 to 0.25 wt % of monopotassium phosphate ($KH_2PO_4$), 0.05 to 0.25 wt % of dipotassium phosphate ($K_2HPO_4$) and residual quantity of water.

The culture in a liquid of step (a) may be conducted under a blue LED light source, and may be conducted with a carbon dioxide concentration maintained at 1,000 to 2,000 ppm.

For example, the culture in a liquid may be conducted for 8 to 13 days at 20 to 25° C., under a blue LED light source, with the pH maintained at 4.5 to 6.0, an illuminance maintained at 0.5 LUX, an air injected at 0.5 to 1.5 kgf/cm$^2$, and carbon dioxide concentration maintained at 1,000 to 2,000 ppm, and preferably, the culture is conducted for 10 days under the condition of 22° C., pH 5.0, 1.0 kgf/cm$^2$, and 1,500 ppm, to attain a high content of an extracellular polysaccharide.

The parent strain for use in step (a) may be a strain obtained by culturing a dominant strain stored in PDA (Potato dextrose agar) medium at 4° C. in PDB (Potato dextrose broth) medium in Erlenmeyer flask using a shaking incubator at a constant temperature of 25° C. for 7 to 9 days. Herein, the amount of the mycelium to be inoculated is preferably about 0.5% (w/v) based on the solution to be cultured. Since a high amount of the mycelia (%/100 mL) does not necessarily result in a high content of the extracellular polysaccharide, the medium composition may be preferably selected such that it provides a condition for maximizing the content of extracellular polysaccharide, rather than the best condition for the growth of mycelia.

The culture medium may be separated and purified into mycelia and an aqueous solution. For the separation and purification, the mycelia may be eliminated from the culture medium using a centrifuge and the remaining solution may be repeatedly purifed using a Multi-Sheet Filter Press and a vibrating membrane separator (PALLSEP), followed by irradiation with UV rays for 1 minute. Also, the solution needs to be sealed and stored after removing oxygen, since the presence of mycelia in the solution results may lead to the growth of the mycelia due to oxygen, which may cause the change in the content of the effective ingredient due to the growth of the mycelia.

In step (b), the mycelial culture medium prepared in step (a) may be vacuum dried or freeze dried to form powders. In order to prevent the loss of an effective substance, the drying is preferably carried out at a temperature of 40° C. or lower, preferably 30° C. or lower, for 48 to 96 hours. In addition, for the drying in step (b), a vacuum freeze dryer is preferably used rather than a vacuum dryer in which a relatively high evaporation temperature is set, in terms of minimizing the change in the content of the effective substance.

In step (c), the dried powders of a mycelial culture medium obtained in step (b) are extracted with a solvent, an extracellular polysaccharide, an effective ingredient according to the present invention, is isolated and prepared. Specifically, 100 mL of distilled water may be added to 5 g of dried powders, and the resultant suspension may be centrifuged (8,000 rpm, 20 min), and then, a 2 to 3-fold amount of extraction solvent may be added to the supernatant, and the resulting solution may be placed in a refrigerator (4° C.) and allowed to stand for 12 hours. The supernatant in the solution which had been allowed to stand may be obtained and centrifuged again (8,000 rpm, 20 min), and the precipitate may be recovered, thereby preparing a crude extracellular polysaccharide. The crude extracellular polysaccharide is preferably vacuum freeze dried at a temperature of 30° C. or lower.

The extraction solvent may be a solvent selected from the group consisting of water, ethanol, methanol, acetone, butanol and ethyl acetate, or a mixture thereof, and preferably, it may be water or 50% (w/w) to 80% (w/w) of aqueous solution of ethanol.

A pharmaceutical composition for antioxidation according to the present invention comprising an extracellular polysaccharide produced by *Ceriporia lacerata* or a mycelial culture medium of *Ceriporia lacerata* containing the same, or dried powders or an extract thereof, as an effective ingredient, may further contain a carrier, an excipient and a diluent which are commonly used.

The extracellular polysaccharide may be comprised in an amount of 0.1 to 80 wt %, preferably 0.1 to 50 wt %, based on the total weight of the composition, and a mycelial culture medium of *Ceriporia lacerata*, or dried powders or an extract thereof may be adequately comprised in an amount which corresponds to the above amount of the extracellular polysaccharide. However, the most preferred effective content of an extracellular polysaccharide or a mycelial culture medium containing the extracellular polysaccharide, or dried powders or an extract thereof may be adequately adjusted according to the method of use and purpose of the pharmaceutical composition.

A pharmaceutical composition according to the present invention can be formulated and used in accordance with a conventional method. Suitable formulations may include, but are not limited to, tablets, pills, powders, granules, sugar-coated tablets, hard or soft capsules, solutions, suspensions or emulsions, injections, suppositories, and the like.

A pharmaceutical composition according to the present invention can be prepared into a suitable formulation using a pharmaceutically inert organic or inorganic carrier. That is, lactose, sucrose, starch or a derivative thereof, talc, calcium carbonate, gelatin, or stearic acid or a salt thereof may be used if the formulation is a tablet, a coated tablet, a sugar-coated tablet or a hard capsule. Also, vegetable oil, wax, fat, or semi-solid or liquid polyol may be used if the formulation is a soft capsule. Furthermore, water, polyol, glycerol, vegetable oil, and the like may be used if the formulation is in the form of a solution or syrup.

A pharmaceutical composition according to the present invention may further comprise a preservative, a stabilizer, a wetting agent, an emulsifier, a solubilizer, a sweetener, a coloring agent, an osmotic pressure regulator, an antioxidant, and the like in addition to the above carrier.

A method of administering a pharmaceutical composition according to the present invention can be easily selected in accordance with the formulation, which may be oral or parenteral administration. The dosage may vary depending on the patient's age, antioxidation, weight, disorder severity, and/or route of administration, but is generally 5 to 500 mg/kg, preferably 100 to 250 mg/kg based on the extracellular polysaccharide, an effective ingredient, which may be administered in one to three divided doses a day. However, such dosage does not limit the scope of the present invention in any way.

A pharmaceutical composition according to the present invention not only provides an excellent antioxidation effect but also shows little toxicity and adverse events, and thus can safely be used as an antioxidant by long-term administration. Therefore, a pharmaceutical composition of the present invention can be used for preventing and treating various disorders requiring antioxidation effect such as, for example, aging, cancer, stroke, Parkinson's disease, heart disorder, ischemia, arteriosclerosis, skin damage, inflammation, rheumatism, autoimmune disorder, and the like.

Furthermore, the present invention provides a health functional food having antioxidation effect, comprising an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium, as an effective ingredient.

A health functional food according to the present invention may be in the form of powders, granules, a tablet, a capsule or a drink, and may be a candy, a chocolate, a drink, a gum, a tea, a vitamin complex, a health supplementary food, and the like.

Herein, an extracellular polysaccharide or a mycelial culture medium containing the same, or dried powders or an extract thereof according to the present invention may be generally comprised in a food in an amount of 0.01 to 50 wt %, preferably 0.1 to 20 wt % based on the total weight of the food, and may be generally comprised in a ratio of 0.02 to 10 g, preferably 0.3 to 1 g based on 100 mL of a health drink composition in the case of a health drink composition.

The food may further comprise a sitologically acceptable food supplementary additive in addition to an extracellular polysaccharide or a mycelial culture medium of *Ceriporia lacerata* containing the same, or dried powders or an extract thereof.

The cosmetic composition according to the present invention may contain any conventional ingredients generally used in cosmetics, for example, additives such as stabilizers, solubilizers, surfactants vitamins, pigments and flavors, and carriers, in addition to an extracellular polysaccharide or a mycelial culture medium of *Ceriporia lacerata* containing the same, or dried powders or an extract thereof, which is an effective ingredient showing antioxidation effect.

The cosmetic composition can be formulated in any form that is generally prepared in the art, for example, solution, suspension, an emulsion, paste, gel, cream, lotion, powder, soap, surfactant-containing cleansing, oil, powdered foundation, emulsified foundation, wax foundation and spray, etc. More specifically, the cosmetic composition can be prepared in the form of soft lotion, nutrition lotion, nutrition cream, massage cream, essence, eye cream, cleansing cream, cleansing foam, cleansing water, pack, spray or powder, but is not limited thereto.

The feed composition according to the present invention can be administered to an animal alone or mixed with other feed composition in an edible carrier. Also, the feed composition can be easily administered to an animal as a top dressing, a mixture with an animal feed or an oral formulation separate from the feed. When the feed composition is administered separately from an animal feed, it can be prepared in an immediate release or sustained release formulation, in combination with a pharmaceutically acceptable edible carrier. Such edible carriers may be either solid or liquid such as, for example, corn starch, lactose, sucrose, soy flakes, peanut oil, olive oil, sesame oil and propylene glycol. When a solid carrier is used, a feed additive can be a tablet, capsule, powder, troche or lozenge or finely dispersible top dressing. When a liquid carrier is used, the feed additive can be a gelatin soft capsule, a syrup or a suspension, an emulsion, or a solution.

An extracellular polysaccharide produced by *Ceriporia lacerata* or a mycelial culture medium of *Ceriporia lacerata* containing the same, or dried powders or an extract thereof, as an effective ingredient according to the present invention can be used as an additive for various drugs, foods, cosmetics and feed for the purpose of exhibiting antioxidation effect, wherein the dosage and the usage form can be appropriately adjusted according to a purpose.

The present invention provides a method for antioxidation comprising administering to a subject in need of antioxidation capacity an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium.

The subject in need of the antioxidation capacity may be a mammal, specifically a human.

Also, the present invention provides a use of an extracellular polysaccharide produced by *Ceriporia lacerata*; a mycelial culture medium of *Ceriporia lacerata* containing the extracellular polysaccharide; dried powders of the mycelial culture medium; or an extract of the mycelial culture medium for preparing a drug for antioxidation.

Such extracellular polysaccharide produced by *Ceriporia lacerata* or a mycelial culture medium of *Ceriporia lacerata* containing the same, or dried powders or an extract thereof was as described above.

Also, the above antioxidation capacity can be used for preventing and treating various disorders requiring antioxidation effect such as, for example, aging, cancer, stroke, Parkinson's disease, heart disorder, ischemia, arteriosclerosis, skin damage, inflammation, rheumatism, autoimmune disorder, and the like.

MODE FOR THE INVENTION

Hereinafter, the present invention will be described in more detail with the following Examples. The following Examples are provided to illustrate the present invention, but the scope of the present invention is not limited thereto.

EXAMPLES

Preparation Example 1. Preparation of Culture Medium of *Ceriporia lacerata*, Dried Powders Thereof; Extract, and Extracellular Polysaccharide (Exopolysaccharide; Hereinafter Referred to as "EPS")

1.1 Preparation of Culture Medium of *Ceriporia lacerata*

*Ceriporia lacerata* isolated from *Quercus serrata* collected at Sangju city, Gyeongbuk province were subcultured to obtain a parent strain which was subsequently freeze-stored at −80° C., and the freeze-stored strain was cultured with 2-3 passages in PDA (Potato dextrose agar) medium (87 plastic bulbs; Difco, Becton Dickinson and Company), and the complete strains of sufficient amount alone were stored in a refrigerator at 4° C. until use. Then, 600 mL of the PDB (Potato dextrose broth) medium (Difco, Becton Dickinson and Company) was placed in an Erlenmeyer flask, and a PDA culture strain was added thereto and shake-cultured for 8 days at 25° C. to obtain a PDB culture strain.

Thereafter, a liquid culture medium containing 1.5 wt % of sugar, 0.5 wt % of glucose, 0.5 wt % of potato starch, 0.25 wt % of sorghum powder, 0.25 wt % of barley powder, 0.75 wt % of soybean flour, 0.05 wt % of magnesium sulfate ($MgSO_4$), 0.05 wt % of monopotassium phosphate ($KH_2PO_4$), 0.05 wt % of dipotassium phosphate ($K_2HPO_4$) and residual quantity of water was sterilized for 20 minutes in a 800 L fermenter at 121° C. and 1.5 kgf/$cm^2$, and then, the medium was cooled to 23° C. and inoculated with 600 mL of the PDB culture strain as a starter. *Ceriporia lacerata* mycelia were liquid-cultured in the medium for 10 days at a constant temperature of 23° C., with the air injected at 0.5 to 1.5 kgf/$cm^2$, under a blue LED light source, at an illuminance of 0.5 LUX, with a carbon dioxide concentration of 2,000 ppm, to prepare the mycelial culture medium of *Ceriporia lacerata*.

1.2 Preparation of Dried Powders of Culture Medium of *Ceriporia lacerata*

The mycelial culture medium of *Ceriporia lacerata* prepared in the Preparation Example 1.1 was freeze-dried by a vacuum freeze dryer at 25° C. for 72 hours to form powders, to prepare the dried powders of mycelial culture medium of *Ceriporia lacerata*.

1.3 Preparation of Extract of Culture Medium of *Ceriporia lacerata*

5 g of the dried powders of the culture medium of *Ceriporia lacerata* prepared in Preparation Example 1.2 was added with 100 mL of distilled water and sufficiently suspended, and then the resulting solution was centrifuged at 8,000 rpm for 20 minutes. The supernatant separated therefrom was mixed with a 2- to 3-fold amount of ethanol and allowed to stand for 12 hours at 4° C. The resultant supernatant was taken and an extract of the mycelial culture medium of *Ceriporia lacerata* was prepared therefrom.

1.4 Preparation of EPS from Culture Medium of *Ceriporia lacerata*

The extract of the culture medium of *Ceriporia lacerata* prepared in Preparation Example 1.3 was further centrifuged at 8,000 rpm for 20 minutes, and then the precipitate was recovered to obtain crude EPS. The crude EPS was vacuum freeze dried in a vacuum freeze dryer for 72 hours at 25° C. to obtain an EPS produced by *Ceriporia lacerata*.

Example 1. Evaluation of EPS Properties

1.1. Molecular Weight Measurement of EPS using Gel Permeation Chromatography (GPC)

The EPS prepared in Preparation Example 1 was dissolved in a solution of 0.1 M $Na_2SO_4$/0.05 M $NaN_3$ (adjusted to pH 4 with glacial acetic acid) to a concentration of 1% (w/v), and then the mixture was centrifuged and the supernatant was isolated and filtered with a 0.45 μm syringe filter and analyzed by GPC.

Specifically, the refractive index of the detector was used for the GPS analysis, OHpak SB 805 HQ (Shodex, Japan) was used for the GPC column, and 0.1 M $Na_2SO_4$/0.05 M $NaN_3$ (adjusted to pH 4 with glacial acetic acid) was used for a mobile phase. The mobile phase was allowed to flow at a flow rate of 1.0 mL/min. Standard curves were generated using dextrans (American Polymer Corporation, USA) with different molecular weights (130, 400, 770 or 1200 kDa), and the molecular weight of EPS was measured using refractive index (RI) measuring instrument Knauer K-2310 (Germany). The measurement conditions are summarized in Table 1 below.

TABLE 1

|  | Measurement of molecular weight |
|---|---|
| HPLC system | Knauer K-501 system |
| Column | OHpak SB 805 HQ (Shodex, Japan) |
| Mobile phase | 0.1M $Na_2SO_4$/0.05M $NaN_3$/pH 4 |
| Flow rate | 1.0 mL/min |
| Measuring instrument | RI (Knauer K-2310) |

As a result, the molecular weight of EPS of the present invention was about 120 kDa.

1.2. Measurement of Sugar and Protein Contents of EPS

The EPS prepared in the Preparation Example 1 was subjected to secondary purification and treated with a protein-hydrolysis enzyme to measure sugar and protein contents.

Specifically, the primary-purified EPS was dissolved in distilled water again and centrifuged at 8,000 rpm for 20 minutes to separate the supernatant, and then a 2- to 3-fold amount of ethanol was added thereto. The mixture was placed in a refrigerator at 4° C. and allowed to stand for 12 hours. Then, the resultant supernatant alone was centrifuged again at 8,000 rpm for 20 minutes, and the precipitate was recovered to obtain a secondary-purified EPS. And the purified EPS was dissolved in distilled water and treated with Alcalase, a protein-hydrolysis enzyme, at a concentration of 0.5% (w/v) at 50° C. for 30 minutes.

The sugar content was measured by the phenol-sulfuric acid method. Specifically, 25 μL of 80% phenol was added to 1 mL of each of the samples diluted at various concentrations, and then 2.5 mL of sulfuric acid was added thereto. The mixture was cooled to room temperature, and then the sugar content was calculated by measuring the absorbance at 465 nm.

Also, the protein content was measured by BCA method (see Smith P K et al., *Analytical Biochemistry*, 150 (1): 76-85 (1985)) and bovine serum albumin was used as a standard.

The sugar contents and protein contents measured as described above are shown in Table 2 below. The sugar content was 45 to 51 wt % and the protein content was 33 to 34 wt %.

TABLE 2

|  | Yield (%) | Total sugar content (%) | Total protein content (%) |
|---|---|---|---|
| EPS | 1.22 ± 0.03 | 45.32 ± 1.41 | 34.17 ± 0.73 |
| Secondary-purified EPS | 0.78 ± 0.01 | 50.49 ± 0.52 | 33.50 ± 2.79 |
| Enzyme-treated EPS* | 0.24 ± 0.06 | 51.39 ± 1.32 | 34.61 ± 1.51 |

*Enzyme treatment: Alkalase 0.5%, 50° C., 30 minutes.
Each value represents mean ± SE (n ≥ 3).

As a result of analyzing sugar content of EPS, it was found that EPS mainly contains mannose, galactose and glucose.

Example 2. Verification of Antioxidation Effect of EPS

2.1. Measurement of DPPH Free Radical Elimination Activity

In order to examine the antioxidation effect of the EPS isolated from the mycelial culture medium of *Ceriporia lacerata*, the free radical elimination activity using DPPH (1,1-diphenyl-2-picryhydrazyl) was measured (see Thaipong Kriengsak., et al., *Journal of Food Composition and Analysis*, vol. 19, pp. 669-675, 2006).

Specifically, the DPPH radical elimination activity was measured by a method in which the DPPH free radical was eliminated by an antioxidant of the sample, resulting in discoloration of the purple color, which is unique color of the radical. 2 uL of EPS was added to each well of a 96-well plate (100 ppm, 200 ppm, 300 ppm, 400 ppm, 500 ppm, and 1,000 ppm) at each concentration and then mixed with 198 uL of 100 uM DPP solution, followed by incubation at room temperature for 30 minutes. Then, the absorbance at 540 nm was measured to determine the amount of remaining DPPH and the DPPH radical elimination activity was examined depending on the concentration. Thereafter, the radical elimination ratio (%) obtained by comparing the absorbance of the samples according to the present Example with that of the control group without DPPH was shown in Table 3 and FIG. 1. The radical elimination ratio (%) was calculated as [1−(absorbance of sample/absorbance of control group)]× 100.

TABLE 3

| | DPPH radical elimination rate (%) | | | | | | |
|---|---|---|---|---|---|---|---|
| | cont | 100 ppm | 200 ppm | 300 ppm | 400 ppm | 500 ppm | 1000 ppm |
| 1 | — | 5.67 | 9.21 | 19.85 | 34.04 | 42.82 | 53.74 |
| 2 | — | 3.54 | 12.76 | 23.40 | 30.49 | 39.31 | 51.54 |
| Average | — | 4.61 | 10.99 | 21.63 | 32.27 | 41.07 | 52.64 |
| SD | — | 1.51 | 2.51 | 2.51 | 2.51 | 2.48 | 1.56 |

As shown in Table 3, it was confirmed that the DPPH radical elimination activity was gradually increased as the concentration of the EPS according to the present invention increased from 100 ppm to 1,000 ppm. Especially, when the concentration of the EPS was 1,000 ppm, the average DPPH radical elimination rate was 52.64%. Therefore, the above results show that the EPS according to the present invention has a strong antioxidation activity.

2.2. Measurement of ABTS Free Radical Elimination Activity

In order to examine the antioxidation effect of the EPS isolated from the mycelial culture medium of *Ceriporia*

*lacerata*, the free radical elimination activity using ABTS (2,2'-azino-bis (3-ethylbenzthiazoline-6-sulfonate) was measured (see Thaipong Kriengsak., et al., *Journal of Food Composition and Analysis*, vol. 19, pp. 669-675, 2006).

Specifically, the ABTS radical elimination activity was measured by a method in which the ABTS free radical generated by a reaction with potassium persulfate was eliminated by an antioxidant substance of the sample, resulting in discoloration of the dark blue-green color, which is unique color of the radical.

2.6 mM potassium sulfate was mixed with 7.4 mM ABTS solution and allowed to react in a dark room for about 24 hours. The mixture was diluted with phosphate buffered saline to show an absorbance of 0.700±0.030 at 732 nm, and then mixed with EPS at the concentrations of 100 ppm, 200 ppm, 300 ppm, 400 ppm, 500 ppm and 1,000 ppm, and reacted in a dark space for 10 minutes. Then, the absorbance at 732 nm was measured to determine the amount of remaining ABTS. Thereafter, the radical elimination ratio (%) obtained by comparing the absorbance of the samples according to the present example with that of the control group without ABTS was shown in Table 4 and FIG. 2. The radical elimination ratio (%) was calculated as [1−(absorbance of sample/absorbance of control group)]×100.

TABLE 4

| | ABTS radical elimination rate (%) | | | | | |
|---|---|---|---|---|---|---|
| | cont | 100 ppm | 200 ppm | 300 ppm | 400 ppm | 500 ppm | 1000 ppm |
| 1 | — | 1.50 | 4.09 | 10.65 | 17.89 | 18.76 | 35.61 |
| 2 | — | 1.08 | 5.85 | 16.21 | 15.37 | 20.80 | 39.72 |
| Average | — | 1.29 | 4.97 | 13.43 | 16.63 | 19.78 | 37.67 |
| SD | — | 0.30 | 1.24 | 3.93 | 1.78 | 1.44 | 2.91 |

As shown in Table 4, it was confirmed that the absorbance of the samples decreased and ABTS radical elimination activity gradually increased as the concentration of the EPS according to the present invention increased from 100 ppm to 1,000 ppm. Especially, when the concentration of the EPS was 1,000 ppm, the average ABTS radical elimination rate was 37.67%, which indicates a strong antioxidation activity. Therefore, the above results show that the EPS according to the present invention has a strong antioxidation activity.

The invention claimed is:

1. A method comprising administering to a subject in need of antioxidation capacity a composition comprising at least one of (a)-(c):
   (a) a mycelial culture medium of *Ceriporia lacerata* containing an extracellular polysaccharide produced by the *Ceriporia lacerata*;
   (b) dried powders of the mycelial culture medium of *Ceriporia lacerata* of (a); and
   (c) an extract of the mycelial culture medium of *Ceriporia lacerata* of (a).

2. The method of claim 1, wherein the extracellular polysaccharide produced by *Ceriporia lacerata* contains mannose, galactose, and glucose.

3. The method of claim 1, wherein the mycelial culture medium of *Ceriporia lacerata* containing an extracellular polysaccharide produced by the *Ceriporia lacerata* is prepared by a preparation method comprising a step of culturing mycelia of *Ceriporia lacerata* in a liquid to prepare the mycelial culture medium of *Ceriporia lacerata*,
   wherein the liquid comprises sugar, glucose, starch, sorghum powder, barley powder, soybean flour, magnesium sulfate ($MgSO_4$), monopotassium phosphate ($KH_2PO_4$), dipotassium phosphate ($K_2HPO_4$) and water.

4. The method of claim 3, wherein the liquid has a pH of 4.5 to 6.0.

5. The method of claim 3, wherein the culturing in a liquid is conducted under a blue LED light source with a carbon dioxide concentration maintained at 1,000 to 2,000 ppm.

6. The method of claim 1, wherein the extracellular polysaccharide is comprised in an amount of 0.1 to 80 wt % based on the total weight of the composition comprising at least one of (a)-(c).

7. The method of claim 1, wherein the composition is a pharmaceutical composition.

8. The method of claim 1, wherein the composition is a food in a form selected from the group consisting of a candy, a chocolate, a drink, a gum, a tea, a vitamin complex, and a health supplementary food.

9. The method of claim 1, wherein the composition is a cosmetic composition.

10. The method of claim 1, wherein the composition is a feed composition.

11. The method of claim 8, wherein the at least one of (a)-(c) is included in an amount of 0.01 to 50 wt % based on the total weight of the food.

* * * * *